(12) United States Patent
Ikeda et al.

(10) Patent No.: US 7,375,081 B2
(45) Date of Patent: May 20, 2008

(54) THERAPEUTIC COMBINATION OF A PNEUMOCANDIN DERIVATIVE AND AN ANTIFUNGAL AGENT

(75) Inventors: Fumiaki Ikeda, Katano (JP); Kazumi Otomo, Ibaraki (JP); Yoshimi Wakai, Toyonaka (JP); Satoru Matsumoto, Amagasaki (JP)

(73) Assignee: Astellas Pharma Inc., Tokyo (JP)

( * ) Notice: Subject to any disclaimer, the term of this patent is extended or adjusted under 35 U.S.C. 154(b) by 227 days.

(21) Appl. No.: 11/038,155

(22) Filed: Jan. 21, 2005

(65) Prior Publication Data

US 2005/0124536 A1 Jun. 9, 2005

Related U.S. Application Data

(63) Continuation of application No. 09/926,679, filed on Nov. 30, 2001, now Pat. No. 6,875,740, which is a continuation of application No. PCT/JP00/03340, filed on May 24, 2000.

(30) Foreign Application Priority Data

May 31, 1999 (AU) .................................... PQ0663

(51) Int. Cl.
*A61K 38/00* (2006.01)
*A61K 31/70* (2006.01)
*C12P 21/06* (2006.01)

(52) U.S. Cl. .................... 514/9; 514/8; 514/11; 514/23; 514/49; 514/383; 530/317; 435/68.1; 435/231

(58) Field of Classification Search ............. 514/9, 514/8, 11, 23, 49, 383; 530/317; 435/68.1, 435/231.1

See application file for complete search history.

(56) References Cited

U.S. PATENT DOCUMENTS 5,030,619 A 7/1991 Hector
2004/0023858 A1 2/2004 Ikeda et al.

FOREIGN PATENT DOCUMENTS

WO  WO 96/11210  4/1996
WO  WO 98/10782  3/1998

OTHER PUBLICATIONS

S. P. Franzot, et al., Antimicrobial Agents and Chemotherapy, vol. 41, No. 2, pp. 331-336, "Pneumocandin L-743,872 Enhances the Activities of Amphotericin B and Fluconazole Against Cryptococcus Neoformans in Vitro", Feb. 1, 1997.
K. Bartizal, et al., Antimocrobial Agents and Chemotherapy, vol. 39, No. 5, pp. 1070-1076, "In Vitro Evaluation of The Pneumocandin Antifungal Agent L-733560, A New Water-Soluble Hybrid of L-705589 and L-731373", May 1, 1995.

*Primary Examiner*—Jon Weber
*Assistant Examiner*—Abdel A Mohamed
(74) *Attorney, Agent, or Firm*—Oblon, Spivak, McClelland, Maier & Neustadt, P.C.

(57) ABSTRACT

There is described antifungal combination use of known antifungal agents such as the azoles or polyenes in combination with a lipopeptide compound antifungal agent. More particularly, the invention relates to antifungal combination use of azoles such as fluconazole, voriconazole, itraconazole, ketoconazole, miconazole, ER 30346 and SCH 56592; polyenes such as amphotericin B, nystatin, liposomal and lipid forms thereof such as Abelcet, AmBisome and Amphocil; purine or pyrimidine nucleotide inhibitors such as flucytosine; or polyoxins such as nikkomycins, in particular nikkomycin Z or nikkomycin X; other chitin inhibitors; elongation factor inhibitors such as sordarin and analogs thereof; mannan inhibitors such as predamycin, bactericidal/permeability-inducing (BPI) protein products such as XMP.97 or XMP.127; or complex carbohydrate antifungal agents such as CAN-296; with a lipopeptide compound [I] as described herein.

12 Claims, No Drawings

THERAPEUTIC COMBINATION OF A PNEUMOCANDIN DERIVATIVE AND AN ANTIFUNGAL AGENT

CROSS-REFERENCE TO RELATED APPLICATIONS

This application is a continuation of application Ser. No. 09/926,679 filed Nov. 30, 2001, now U.S. Pat. No. 6,875,740, which is a continuation of PCT application JP00/03340 filed May 24, 2000, based on Australian priority application No. PQ0663 filed May 31, 1999.

BACKGROUND OF THE INVENTION

TECHNICAL FIELD

The present invention relates to antifungal combination use of known antifungal agents such as the azoles, polyenes and so on in combination with a lipopeptide compound antifungal agent. More particularly, the invention relates to antifungal combination use of azoles such as fluconazole (hereinafter referred to as FLCZ), voriconazole, itraconazole (hereinafter referred to as ITCZ), ketoconazole, miconazole, ER 30346 and SCH 56592; polyenes such as amphotericin B (hereinafter referred to as AMPH-B), nystatin, liposomal and lipid forms thereof such as Abelcet, AmBisome and Amphocil; purine or pyrimidine nucleotide inhibitors such as flucytosine (hereinafter referred to as 5-FC); or polyoxins such as nikkomycins, in particular nikkomycin Z or nikkomycin X; other chitin inhibitors; elongation factor inhibitors such as sordarin and analogs thereof; mannan inhibitors such as predamycin, bactericidal/permeability-inducing (BPI) protein products such as XPM.97 or XMP.127; or complex carbohydrate antifungal agents such as CAN-296; with a lipopeptide compound [I] of the following formula:

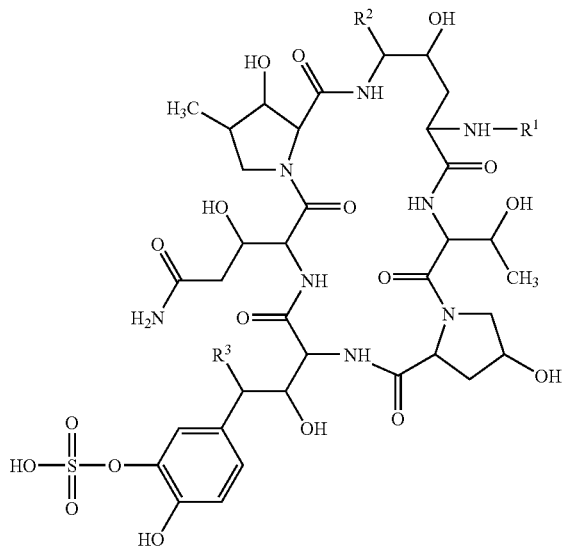

[I]

Wherein $R^1$ is acyl group,
$R^2$ is hydrogen or hydroxy and
$R^3$ is hydrogen or hydroxy,
or a salt thereof.

BACKGROUND ART

There is an increasing need for agents which are effective against opportunistic mycotic infections by such agents as *Cryptococcus, Candida, Aspergillus, Histoplasma, Coccidioides, Paracoccidioides, Blastomyces, Fusarium, Sporothrix, Trichosporon, Rhizopus, Pseudallescheria,* dermatophytes, *Paeciliomyces, Alternaria, Curvularia, Exophiala, Wangiella, Penicillium, Saccharomyces,* Dematiaceous fungi, *pneumocystis carinii* and so on. The present uses, i.e., polyenes, such as amphotericin B, cause severe side effects and azoles, such as fluconazole, are only fungistatic. The lipopeptide compound [I] is cyclic hexapeptide which inhibits cell wall 1,3β-D-glucan synthesis. The lipopeptide compound [I] has shown potent in vivo. activity against *Candida, Pneumocystis carinii, Aspergillus,* as well as the other fungal pathogens listed above.

Combination use with antifungal drugs may provide additional options for treating *Aspergillus* and other fungal pathogens.

Previous studies have evaluated the efficacy of other lipopeptide compounds against *Cryptococcus neoformans* in combination with amphotericin B and fluconazole (Abruzzo et al., Antimicrob. Agents Chemo. 1995, 39:1077-1081 and Bartizal et al., Antimicrob. Agents Chemo. 1995, 39:1070-1076). However, none of these studies have demonstrated the results found using the lipopeptide compound [I].

DISCLOSURE OF THE INVENTION

The present invention relates to antifungal combination use of known antifungal agents such as the azoles, polyenes and so on in combination with a lipopeptide compound antifungal agent. More particularly, the present invention relates to antifungal combination use of azoles such as fluconazole, voriconazole, itraconazole, ketoconazole, miconazole, ER 30346 and SCH 56592; polyenes such as amphotericin B, nystatin, liposomal and lipid forms thereof such as Abelcet, AmBisome and Amphocil; purine or pyrimidine nucleotide inhibitors such as flucytosine; or polyoxins such as nikkomycins, in particular nikkomycin Z or nikkomycin X; other chitin inhibitors; elongation factor inhibitors such as sordarin and analogs thereof; mannan inhibitors such as predamycin, bactericidal/permeability-inducing (BPI) protein products such as XMP.97 or XMP.127; or complex carbohydrate antifungal agents such as CAN-296; with a lipopeptide compound [I] of the following formula:

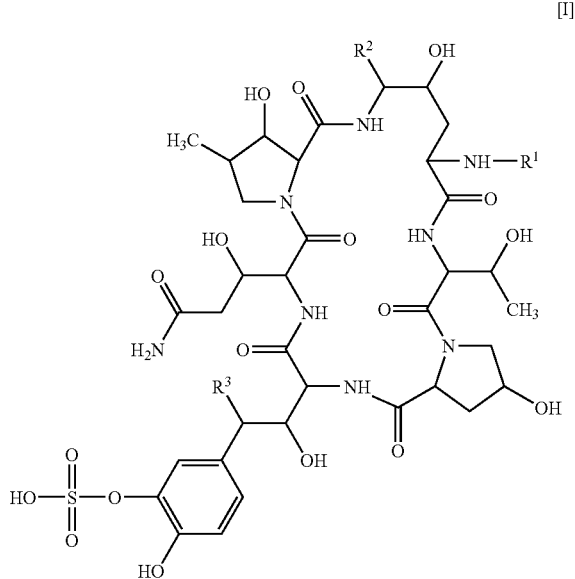

Wherein R¹ is acyl group,
R² is hydrogen or hydroxy and
R³ is hydrogen or hydroxy,
or a salt thereof.

Suitable salt of the lipopeptide compound [I] is a pharmaceutically acceptable and conventional non-toxic salt, and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt;

a salt with an organic base, for example, an organic amine salt (e.g., triethylamine salt, diisopropylethylamine salt, pyridine salt, picoline salt, ethanolamine salt, triethanolamine salt, dicyclohexylamine salt, N,N'-dibenzylethylenediamine salt, etc.);

an inorganic acid addition salt (e.g., hydrochloride hydrobromide, sulfate, phosphate, etc.);

an organic carboxylic sulfonic acid addition salt (e.g., formate, acetate, trifluoroacetate, maleate, tartrate, fumarate, methanesulfonate, benzenesulfonate, toluenesulfonate, etc.);

a salt with a basic or acidic amino acid (e.g., arginine, aspartic acid, glutamic acid, etc.).

It is to be noted that each of the lipopeptide compound [I] may include one or more stereoisomer(s) such as optical isomer(s) and geometrical isomer(s) due to asymmetric carbon atom(s) and double bond(s), and all such isomer(s) and the mixture thereof are included within the scope of the present invention.

The lipopeptide compound [I] or a salt thereof includes solvated compound [e.g., enclosure compound (e.g., hydrate, etc.)].

The lipopeptide compound [I] or a salt thereof includes both its crystal form and non-crystal form.

It should be understood that the lipopeptide compound [I] in the present invention may include the prodrug form.

Suitable example of "acyl group" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows.

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

Aromatic acyl such as aroyl (e.g., benzoyl, toluoyl, naphthoyl, etc.); aroyl which has one or more suitable substituent(s);

ar(lower)alkanoyl [e.g., phenyl($C_1$-$C_6$)alkanoyl (e.g., phenylacetyl, phenylpropanoyl, phenylbutanoyl, phenylisobutanoyl, phenylpentanoyl, phenylhexanoyl, etc.), naphthyl($C_1$-$C_6$)alkenoyl (e.g., naphthylacetyl, naphthylpropenoyl, naphthylbutanoyl, etc.), etc.];

ar(lower)alkenoyl [e.g., phenyl($C_3$-$C_6$)alkenoyl (e.g., phenylpropenoyl, phenylbutenoyl, phenylmethacryloyl, phenylpentanoyl, phenylhexenoyl, etc.), naphthyl ($C_3$-$C_6$) alkenoyl (e.g., naphthylpropenoyl, naphthylbutenoyl, etc.), etc.];

ar(lower)alkoxycarbonyl [e.g., phenyl($C_1$-$C_6$)alkoxycarbonyl (e.g., benzyloxycarbonyl, etc.), fluorenyl($C_1$-$C_6$) alkoxy-carbonyl (e.g., fluorenylmethyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.); arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

Heterocyclic aryl such as heterocycliccarbonyl; heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like.

Among them, more preferred "acyl group" is aroyl which has one or more suitable substituent(s).

Suitable example of "suitable substituent(s)" in the term of "aroyl which has one or more suitable substituent(s)" may be heterocyclic group substituted with aryl having lower alkoxy, heterocyclic group substituted with aryl having lower alkoxy(lower)alkoxy, heterocyclic group substituted with aryl having lower alkoxy(higher)alkoxy, heterocyclic group substituted with aryl having cyclo(lower)alkyloxy, heterocyclic group substituted with aryl having heterocyclic group, heterocyclic group substituted with cyclo(lower) alkyl having cyclo(lower)alkyl, heterocyclic group substituted with aryl having aryl substituted with lower alkoxy (lower)alkoxy, heterocyclic group substituted with aryl having heterocyclic group substituted with cyclo(lower)alkyl;

in which the preferred one may be unsaturated 3 to 8-membered heteromonocyclic group containing 1 to 2 oxygen atom(s) and 1 to 3 nitrogen atom(s) substituted with phenyl having ($C_4$-$C_6$)alkoxy, unsaturated condensed heterocyclic group containing 1 or 2 sulfur atom(s) and 1 to 3 nitrogen atom(s) substituted with phenyl having ($C_4$-$C_6$) alkoxy, unsaturated 3 to 8-membered heteromonocyclic group containing 1 or 2 sulfur atom(s) and 1 to 3 nitrogen atom(s) substituted with phenyl having ($C_1$-$C_4$)alkoxyalkoxy-($C_4$-$C_6$)alkoxy, unsaturated 3 to 8-membered heteromonocyclic group containing 1 or 2 sulfur atom(s) and 1 to 3 nitrogen atom(s) substituted with phenyl having ($C_1$-$C_4$) alkoxy($C_7$-$C_{14}$)alkoxy, saturated 3 to 8-membered heteromonocyclic group containing 1 to 4 nitrogen atom(s) substituted with phenyl having ($C_1$-$C_4$)alkoxy($C_7$-$C_{14}$)alkoxy, unsaturated condensed heterocyclic group containing 1 or 2 sulfur atom(s) and 1 to 3 nitrogen atom(s) substituted with phenyl having cyclo($C_4$-$C_6$)alkyloxy, unsaturated condensed heterocyclic group containing 1 or 2 sulfur atom(s) and 1 to 3 nitrogen atom(s) substituted with phenyl saturated 3 to 8-membered heteromonocyclic group containing 1 or 2 oxygen atom(s) and 1 to 3 nitrogen atom(s), saturated 3 to 8-membered heteromonocyclic group containing 1 to 4 nitrogen atom(s) substituted with cyclo($C_4$-$C_6$)alkyl having cyclo($C_4$-$C_6$)alkyl, unsaturated 3 to 8-membered heteromonocyclic group containing 1 or 2 sulfur atom(s) and 1 to 3 nitrogen atom(s) substituted with phenyl having phenyl substituted with ($C_1$-$C_4$)alkoxy($C_1$-$C_4$)alkoxy, unsaturated 3 to 8-membered heteromonocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) substituted with cyclo($C_4$-$C_6$)alkyl, unsaturated condensed heterocyclic group containing 1 or 2 sulfur atom(s) and 1 to 3 nitrogen atom(s) substituted with phenyl having saturated 3 to 8-membered heteromonocyclic group containing 1 to 4 nitrogen atom(s) having cyclo($C_4$-$C_6$)alkyl, etc.

Among them, the most preferred one may be isoxazolyl substituted with phenyl having pentyloxy, imidazothiadiazolyl substituted with phenyl having pentyloxy, thiadiazolyl substituted with phenyl having methoxyhexyloxy, thiadiazolyl substituted with phenyl having methoxyoctyloxy, thiadiazolyl substituted with phenyl having methoxyheptyloxy, imidazothiadiazolyl substituted with phenyl having cyclohexyloxy, imidazothiadiazolyl substituted with phenyl having dimethylmorpholino, piperazinyl substituted with phenyl having methoxyheptyloxy, piperazinyl substituted with phenyl having methoxyoctyloxy, piperazinyl substituted with cyclohexyl having cyclohexyl, thiadiazolyl substituted with phenyl having phenyl substituted with methoxyethoxy, thiadiazolyl substituted with phenyl having phenyl substituted with methoxybutoxy, thiadiazolyl substituted with phenyl having phenyl substituted with ethoxypropoxy, imidazothiadiazolyl substituted with phenyl having piperazinyl substituted with cyclohexyl, imidazothiadiazolyl substituted with phenyl having piperazinyl substituted with cyclohexyl.

The more suitable example of "acyl group" of $R^1$ may be benzoyl which has isoxazolyl substituted with phenyl having pentyloxy, benzoyl which has imidazolthiadiazolyl substituted with phenyl having pentyloxy, benzoyl which has thiadiazolyl substituted with phenyl having methoxyhexyloxy, benzoyl which has thiadiazolyl substituted with phenyl having methoxyoctyloxy, benzoyl which has thiadiazolyl substituted with phenyl having methoxyheptyloxy, benzoyl which has imidazothiadiazolyl substituted with phenyl having cyclohexyloxy, benzoyl which has imidazothiadiazolyl substituted with phenyl having dimethylmorpholino, benzoyl which has piperazinyl substituted with phenyl having methoxyheptyloxy, benzoyl which has piperazinyl substituted with phenyl having methoxyoctyloxy, benzoyl which has piperazinyl substituted with cyclohexyl having cyclohexyl, benzoyl which has thiadiazolyl substituted with phenyl having phenyl substituted with methoxyethoxy, benzoyl which has thiadiazolyl substituted with phenyl having phenyl substituted with methoxybutoxy, benzoyl which has thiadiazolyl substituted with phenyl having phenyl substituted with ethoxypropoxy, benzoyl which has imidazothiadiazolyl substituted with phenyl having piperazinyl substituted with cyclohexyl, benzoyl which has imidazothiadiazolyl substituted with phenyl having piperazinyl substituted with cyclohexyl.

The lipopeptide compound (I), its preparation, its dosage, etc. are disclosed in U.S. Pat. Nos. 5,569,646, 5,569,946 and WO 96/11210, the disclosures of which are incorporated herein by reference.

The azole, polyene or other antifungal agent may be administered orally or parenterally. The lipopeptide compound [I] is preferably administered parenterally, but is not limited to that route, and may also be administered by other routes such as oral, intramuscular or subcutaneous, and may be administered simultaneously, separately, sequentially in combination with the azole, polyene or other antifungal agent.

In more details, the antifungal combination use of the present invention is effective, particularly against the following fungi.

*Acremonium;*
*Absidia* (e.g., *Absidia corymbifera*, etc);
*Aspergillus* (e.g., *Aspergillus clavatus, Aspergillus flavus, Aspergillus fumigatus, Aspergillus nidulans, Aspergillus niger, Aspergillus terreus, Aspergillus versicolor*, etc);
*Blastomyces* (e.g., *Blastomyces dermatitidis*, etc);
*Candida* (e.g., *Candida albicans, Candida glabrata, Candida guilliermondii, Candida kefyr, Candida krusei, Candida parapsilosis, Candida stellatoidea, Candida tropicalis, Candida utilis*, etc.);
*Cladosporium* (e.g., *Cladosporium trichoides*, etc);
*Coccidioides* (e.g., *Coccidioides immitis*, etc);
*Cryptococcus* (e.g., *Cryptococcus neoformans*, etc);
*Cunninghamella* (e.g., *Cunninghamella elegans*, etc);
*Dermatophyte;*
*Exophiala* (e.g., *Exophiala dermatitidis, Exophiala spinifera*, etc).
*Epidermophyton* (e.g., *Epidermophyton floccosum*, etc);
*Fonsecaea* (e.g., *Fonsecaea pedrosoi*, etc);
*Fusarium* (e.g., *Fusarium solani*, etc);
*Geotrichum* (e.g., *Geotrichum candiddum*, etc);
*Histoplasma* (e.g., *Histoplasma capsulatum* var. *capsulatum*, etc);
*Malassezia* (e.g., *Malassezia furfur*, etc);
*Microsporum* (e.g., *Microsporum canis, Microsporum gypseum*, etc);
*Mucor;*
*Paracoccidioides* (e.g., *Paracoccidioides brasiliensis*, etc);
*Penicillium* (e.g., *Penicillium marneffei*, etc);
*Phialophora;*
*Pneumocystis* (e.g., *Pneumocystis carinii*, etc);
*Pseudallescheria* (e.g., *Pseudallescheria boydii*, etc);
*Rhizopus* (e.g., *Rhizopus microsporus* var. *rhizopodiformis, Rhizopus oryzae*, etc);
*Saccharomyces* (e.g., *Saccharomyces cerevisiae*, etc);
*Scopulariopsis;*
*Sporothrix* (e.g., *Sporothrix schenckii*, etc);
*Trichophyton* (e.g., *Trichophyton mentagrophytes, Trichophyton rubrum*, etc);

*Trichosporon* (e.g., *Trichosporon asahii, Trichosporon cutaneum*, etc).

The above fungi are well known to cause various infection diseases in skin, hair, nail, oral mucosa, gastrointestinal tract, lung, endocardium, brain, meninges, urinary organ, vaginal protion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, and so on.

Therefore, the combination use of the present invention are useful for preventing and treating various infectious diseases, such as dermatophytosis (e.g., trichophytosis, etc), pityriasis versicolor, candidiasis, cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and so on.

The invention is further described in connection with the following non-limiting examples.

EXAMPLES

Test Compound

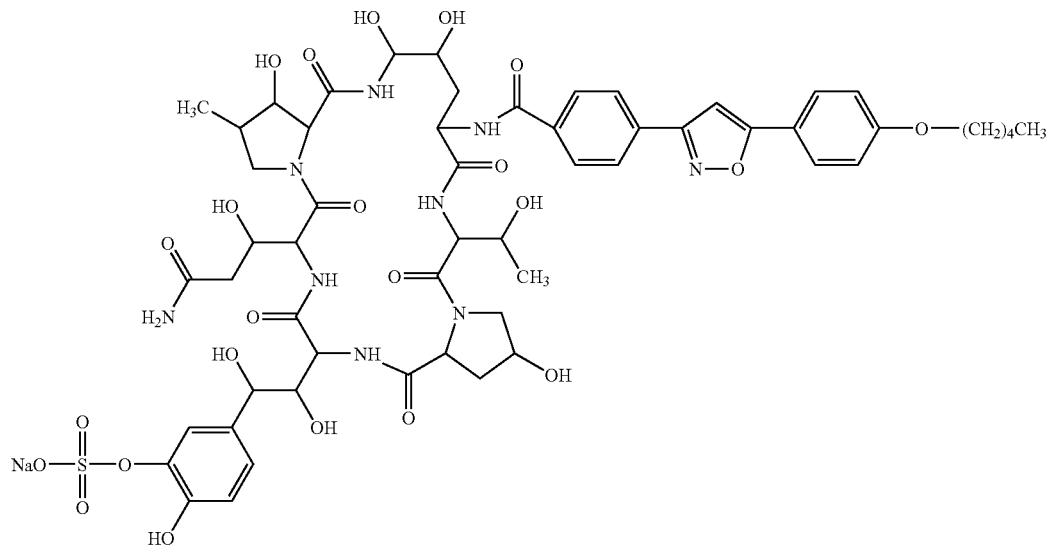

Test Method

The broth microdillution method using RPMI medium (pH 7.0) was used, comparing the each drug alone (Test Compound, AMPH-B, ITCZ, Nikkomycin X and 5-FC) and combined for each clinical isolates of *Aspergillus fumigatus*. A combination of drug concentrations was evaluated by the checkerboard method.

All tubes were examined macroscopically for growth and compared to a control (no drug). MIC was visually determined as the lowest concentration resulting in prominent decrease in turbidity compared to controls.

The Fractional Inhibitory Concentration (FIC) for each drug in mixture wells was compared to the MIC for each drug alone. The FIC index was calculated from the sum of the FICs for the two drugs. A quantitative expression of the interaction for inhibition is as follows:

Synergy ≦ 0.5;

Test Result

In vitro combination with Test Compound and AMPH-B against *A. fumigatus*

| | MIC (µg/ml) | | | | |
| --- | --- | --- | --- | --- | --- |
| Organism | Test Compound Alone | Test Compound Combination | AMPH-B Alone | AMPH-B Combination | FIC Index |
| *A. fumigatus* 8004 | 0.0313 | 0.0078 | 2 | 0.5 | 0.50 |

In vitro combination with Test Compound and ITCZ against *A. fumigatus*

| | MIC (µg/ml) | | | | |
| --- | --- | --- | --- | --- | --- |
| Organism | Test Compound Alone | Test Compound Combination | ITCZ Alone | ITCZ Combination | FIC Index |
| *A. fumigatus* 8008 | 0.0313 | 0.0078 | 0.5 | 0.125 | 0.50 |

In vitro combination with Test Compound and Nikkomycin X against *A. fumigatus*

| | MIC (μg/ml) | | | | |
|---|---|---|---|---|---|
| Organism | Test Compound Alone | Test Compound Combination | Nikkomycin X Alone | Nikkomycin X Combination | FIC Index |
| *A. fumigatus* FP1923 | 0.0039 | ≦0.001 | 128 | 4 | 0.28 |

In vitro combination with Test Compound and 5-FC against *A. fumigatus*

| | MIC (μg/ml) | | | | |
|---|---|---|---|---|---|
| Organism | Test Compound Alone | Test Compound Combination | 5-FC Alone | 5-FC Combination | FIC Index |
| *A. fumigatus* FP1990 | 0.0078 | 0.002 | >32 | 8 | 0.38 |

From the results of the above example, synergy effect of efficacy was observed with combination of the lipopeptide compound [I] and amphotericin B, itraconazole, Nikkomycin X or 5-FC at certain concentrations. No antagonism of efficacy with amphotericin B, itraconazole, Nikkomycin X or 5-FC in combination with the lipopeptide compound [I] also was seen.

We also have examined in vitro combination with the lipopeptide compound [I] and amphotericin B or itraconazole against other fungi such as *C. albicans*, *C. neoformans* and so on. From the result, synergy effect of efficacy was observed with such combination use.

Given the above disclosure, it is confirmed that combination using various antifungal agents and the lipopeptide compound. [I] is effective against fungal infections caused by the fungal pathogens. Accordingly, it is intended that the above examples should be construed as illustrative and that the invention disclosed herein should be limited only by the following claims.

The invention claimed is:

1. A method, for treatment or inhibition of an infectious disease, which comprises:

administering an effective amount of a lipopeptide compound [I] of the following formula:

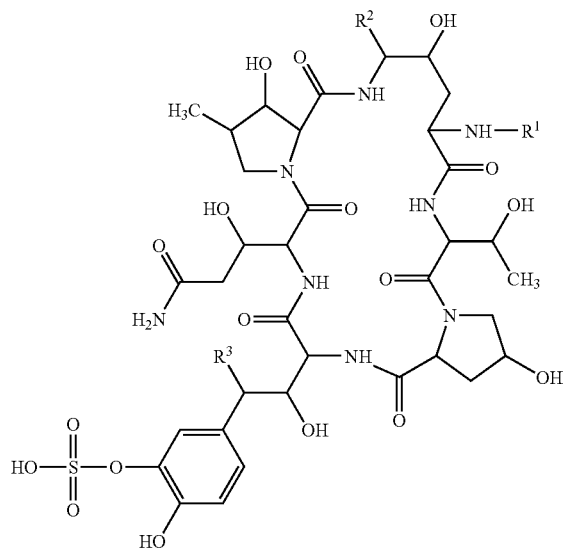

wherein $R^1$ is acyl group, $R^2$ is hydrogen or hydroxy and $R^3$ is hydrogen or hydroxy, or a pharmaceutically acceptable salt thereof, in combination with voriconazole, to a subject suffering from infection by *Aspergillus fumigatus*.

2. The method of claim 1, wherein the infectious disease is aspergillosis.

3. The method of claim 1, wherein the pharmaceutically acceptable salt of the lipopeptide compound [I] is formed from an inorganic base.

4. The method of claim 1, wherein the pharmaceutically acceptable salt of the lipopeptide compound [I] is formed from an organic base.-

5. The method of claim 1, wherein the lipopeptide compound [I] is

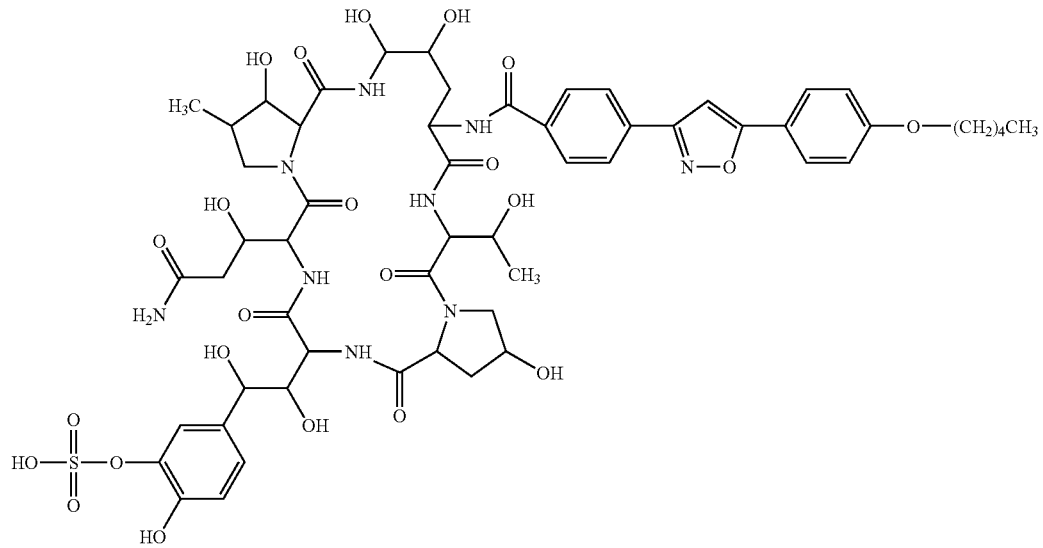

or a salt thereof.

6. A pharmaceutical composition, for the prophylactic and/or therapeutic treatment of the infectious diseases, which comprises:
a therapeutically effective combination of the lipopeptide compound [I] in claim 1 with voriconazole and optionally pharmaceutically carriers or excipients, for the prophylactic and/or therapeutic treatment of infectious disease caused by *Aspergillus fumigatus*.

7. The method of claim 1, wherein said acyl group is aliphatic acyl, aromatic acyl, arylaliphatic acyl or heterocyclicaliphatic acyl.

8. The method of claim 7, wherein said aliphatic acyl is alkanoyl selected from the group consisting of formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl selected from the group consisting of methoxycarbonyl, ethoxycarbonyl, t-butoxycarbonyl, t-pentyloxycarbonyl and heptyloxycarbonyl; alkylsulfonyl selected from the group consisting of methylsulfonyl and ethylsulfonyl; or alkoxysulfonyl selected from the group consisting of methoxysulfonyl or ethoxysulfonyl.

9. The method of claim 7, wherein said aromatic acyl is aroyl selected from the group consisting of benzoyl, toluoyl or naphthoyl; substituted aroyl phenyl($C_1$-$C_6$)alkanoyl selected from the group consisting of phenylacetyl, phenylpropanoyl, phenylbutanoyl, phenylisobutanoyl, phenylpentanoyl, phenylhexanoyl; naphthyl($C_1$-$C_6$)alkanoyl selected from the group consisting of naphthylacetyl, naphthylpropanoyl and naphthylbutanoyl; phenyl($C_3$-$C_6$)alkenoyl selected from the group consisting of phenylpropenoyl, phenylbutenoyl, phenylmethacryloyl, phenylpentanoyl and phenylhexenoyl; naphthyl($C_3$-$C_6$)alkenoyl selected from the group consisting of naphthylpropenoyl and naphthylbutenoyl; phenyl($C_1$-$C_6$)alkoxycarbonyl; fluorenyl($C_1$-$C_6$) alkoxycarbonyl aryloxycarbonyl selected from the group consisting of phenoxycarbonyl and naphthyloxycarbonyl; aryloxy(lower)alkanoyl selected from the group consisting of phenoxyacetyl and phenoxypropionyl; arylcarbamoyl; arylthiocarbamoyl; arylglyoxyloyl selected from the group consisting of phenylglyoxyloyl and naphthylglyoxyloyl; or arylsulfonyl selected from the group consisting of phenylsulfonyl and p-tolylsulfonyl.

10. The method of claim 7, wherein said heterocyclicaliphaticacyl is heterocyclic(lower)alkanoyl selected from the group consisting of heterocyclicacetyl, heterocyclicpropanoyl, heterocyclicbutanoyl, heterocyclicpentanoyl and heterocyclichexanoyl; heterocyclic(lower)alkenoyl selected from the group consisting of heterocyclicpropenoyl, heterocyclicbutenoyl, heterocyclicpentenoyl and heterocyclichexenoyl; or heterocyclicglyoxyloyl.

11. The method of claim 7, wherein said acyl group is aroyl substituted with at least one heterocyclic group substituted by loweralkoxyaryl, at least one heterocyclic group substituted by lower alkoxy(lower)alkoxyaryl, at least one heterocyclic group substituted by lower alkoxy(higher)alkoxyaryl, at least one heterocyclic group substituted by cyclo(lower)alkoxyaryl, at least one heterocyclic group substituted by heterocyclicaryl, at least one heterocyclic group substituted by cyclo(lower)alkylcyclo(lower)alkyl, at least one heterocyclic group substituted by aryl substituted by loweralkoxy(lower)alkoxyaryl or at least one heterocyclic group substituted by aryl having a cyclo(lower)alkyl heterocyclic group.

12. The method of claim 7, wherein said acyl group of $R^1$ is benzoyl substituted by pentyloxyphenylisoxazolyl, benzoyl substituted by pentyloxyphenylimidazothiadiazolyl, benzoyl substituted by methoxyhexyloxyphenylthiadiazolyl, benzoyl substituted by methoxyoctyloxyphenylthiadiazolyl, benzoyl substituted by methoxyheptyloxyphenylthiadiazoyl, benzoyl substituted by cyclohexyloxyphenylimidazothiadiazolyl, benzoyl substituted by dimethylmorpholino phenylimidazothiadiazolyl, benzoyl substituted by methoxyheptyloxyphenylpiperazinyl, benzoyl substituted by methoxyoctyloxyphenylpiperazinyl, benzoyl substituted by cyclohexylcyclohexylpiperazinyl, benzoyl substituted by methoxyethoxyphenylphenylthiadiazolyl, benzoyl substituted by methoxybutoxyphenylphenylthiadiazolyl, benzoyl substituted by ethoxypropoxyphenylphenylthiadiazolyl, or benzoyl substituted by cyclohexylpiperazinylphenylimidazothiadiazolyl.

* * * * *

UNITED STATES PATENT AND TRADEMARK OFFICE
CERTIFICATE OF CORRECTION

PATENT NO. : 7,375,081 B2  Page 1 of 1
APPLICATION NO. : 11/038155
DATED : May 20, 2008
INVENTOR(S) : Fumiaki Ikeda et al.

It is certified that error appears in the above-identified patent and that said Letters Patent is hereby corrected as shown below:

Column 11, Claim 9, lines 60-61,
  "consisting of phenylacetyl, phenyipropanoyl, phenylbutanoyl,"
    should read -- consisting of phenylacetyl, phenylpropanoyl, phenylbutanoyl, --;
      line 62, "phenyihexanoyl; naphthyl($C_1$-$C_6$)alkanoyl"
    should read -- phenylhexanoyl; naphthyl($C_1$-$C_6$)alkanoyl --;
      line 65, "consisting of phenyipropenoyl,"
    should read -- consisting of phenylpropenoyl, --;
      line 67, "phenylpentanoyl and phenyihexenoyl;"
    should read -- phenylpentanoyl and phenylhexenoyl; --.

Column 12, Claim 9, line 32, "fluorenyl($C_1$ -$C_6$)"
    should read -- fluorenyl($C_1$ -$C_6$) --.

Signed and Sealed this

Twenty-third Day of December, 2008

JON W. DUDAS
*Director of the United States Patent and Trademark Office*